US012582299B2

(12) United States Patent
Buch

(10) Patent No.: US 12,582,299 B2
(45) Date of Patent: Mar. 24, 2026

(54) ENDOSCOPE COMPRISING A BENDING SECTION HAVING INDIVIDUAL SEGMENTS

(71) Applicant: AMBU A/S, Ballerup (DK)

(72) Inventor: Ken Henrik Buch, Vordingbord (DK)

(73) Assignee: AMBU A/S, Ballerup (DK)

( * ) Notice: Subject to any disclaimer, the term of this patent is extended or adjusted under 35 U.S.C. 154(b) by 344 days.

(21) Appl. No.: 18/200,769

(22) Filed: May 23, 2023

(65) Prior Publication Data

US 2023/0380672 A1     Nov. 30, 2023

(30) Foreign Application Priority Data

May 24, 2022     (EP) ..................................... 22175217

(51) Int. Cl.
*A61B 1/005*          (2006.01)
*A61B 1/008*          (2006.01)
*A61M 25/01*          (2006.01)

(52) U.S. Cl.
CPC ............ *A61B 1/0055* (2013.01); *A61B 1/008* (2013.01); *A61M 25/0138* (2013.01)

(58) Field of Classification Search
CPC ... A61B 1/0055; A61B 1/008; A61M 25/0138
See application file for complete search history.

(56) References Cited

U.S. PATENT DOCUMENTS 3,583,393 A      6/1971   Takahashi
5,749,828 A  *   5/1998   Solomon .............. A61B 1/0055
                                                              600/141

(Continued)

FOREIGN PATENT DOCUMENTS

CN          107334449 A      11/2017
CN          111700578 A  *   9/2020   ........... A61B 1/0057

(Continued)

OTHER PUBLICATIONS

European Search Report and Search Opinion received for EP Application No. 22175217.3, mailed on Nov. 15, 2022, 8 pages.

*Primary Examiner* — Michael J Carey
*Assistant Examiner* — Megan Elizabeth Monahan
(74) *Attorney, Agent, or Firm* — Faegre Drinker Biddle & Reath LLP

(57) ABSTRACT

An endoscope including a handle and an insertion cord with a bending section having intermediate segments, the intermediate segments including first intermediate segments and second intermediate segments being arranged alternately one after the other in a proximal-distal direction. Hinges between the first intermediate segments and the second intermediate segments are formed by hinge protrusions engaging in hinge recesses. Steering wires run on the inner circumferential side of the first intermediate segments and on the outer circumferential side in axially extending grooves of the second intermediate segments and keep the alternately arranged first intermediate segments and second intermediate segments together. The first intermediate segments comprise stabilizing protrusions arranged and accommodated in the axially extending grooves in the second intermediate segments, in which the steering wires run.

24 Claims, 7 Drawing Sheets

(56)     References Cited

U.S. PATENT DOCUMENTS

| | | | |
|---|---|---|---|
| 5,759,151 A | 6/1998 | Sturges | |
| 5,807,241 A | 9/1998 | Heimberger | |
| 7,250,027 B2 | 7/2007 | Barry | |
| 9,113,783 B2 | 8/2015 | Suehara | |
| 2007/0049800 A1* | 3/2007 | Boulais ................. | A61B 1/008 |
| | | | 600/141 |
| 2008/0177144 A1* | 7/2008 | Otawara ............ | G02B 23/2476 |
| | | | 600/168 |
| 2009/0264817 A1* | 10/2009 | Flach ................ | A61M 25/0147 |
| | | | 604/95.04 |
| 2015/0066033 A1* | 3/2015 | Jorgensen ............. | A61B 34/71 |
| | | | 606/170 |
| 2020/0107898 A1 | 4/2020 | Kim et al. | |
| 2021/0219821 A1* | 7/2021 | Appling ............... | A61B 1/0056 |

FOREIGN PATENT DOCUMENTS

| | | |
|---|---|---|
| CN | 212281292 U | 1/2021 |
| EP | 2581031 A1 | 4/2013 |
| WO | 2021/146682 A1 | 7/2021 |

* cited by examiner

ENDOSCOPE COMPRISING A BENDING SECTION HAVING INDIVIDUAL SEGMENTS

CROSS-REFERENCE TO RELATED APPLICATIONS

This application claims priority from and the benefit of European Patent Application No. EP 22175217.3, filed May 24, 2022; said application is incorporated by reference herein in its entirety.

The following commonly-owned patents and applications are incorporated herein by reference in their entirety: U.S. patent application Ser. No. 18/037,958, filed May 19, 2023, U.S. Pat. No. 11,166,622, issued Nov. 9, 2021, U.S. Pat. No. 11,166,624, issued Nov. 9, 2021, U.S. Pat. No. 11,291,355, issued Apr. 5, 2022, and U.S. Pat. No. 11,622,674, issued Apr. 11, 2023.

TECHNICAL FIELD

The present disclosure relates to an endoscope with a bending section comprising bending segments. More specifically, the disclosure relates to a bending section having separate annular or tubular segments.

BACKGROUND

Endoscopes, including specialized versions thereof, such as bronchoscopes, arthroscopes, colonoscopes, laparoscopes, gastroscopes, duodenoscopes and ureteroscopes are well known from the related art and are used for visual examination and diagnosis of hollow organs and body cavities, as well as to assist in surgery, e.g. for a targeted tissue sampling. Both reusable and disposable (i.e. single-use) endoscopes are known from the related art. Known endoscopes usually comprise an handle via which an operator/user can hold and control the endoscope. An insertion cord comprising an insertion tube, an actively bendable bending section, which is a section of increased flexibility, and a distal tip unit is usually connected to the handle. The insertion cord is configured to be inserted into the hollow organs and body cavities of a patient.

Known endoscopes often contain steering wires that are pulled and released to bend the flexible bending section of the endoscope and tilt the distal tip unit. To achieve a bending of the bending section, a rotating force being applied to e.g. a steering wheel or a lever provided at the proximal handle by a user may be transmitted into a pulling force acting on the steering wires in an axial direction of the steering wires.

Single-use endoscopes are already known which have a bending section comprising a bending section body molded in one single piece or two single pieces of a polymer material. The bending section body of such a single-use endoscope comprises a number of rigid bending segments kept together by bendable hinges. Between adjacent bending segments of the bending section body two or three hinge members or hinge parts may be provided, which are arranged approximately diametrically opposed with respect to a center axis of the bending section body. The hinge members may e.g. be formed as foil hinges, i.e. as short strips of bendable bridges of material between adjacent bending segments allowing the material to bend in an elastic manner between adjacent bending segments.

Bending sections assembled from a plurality of separate annular or tubular bending segments as known in the related art have a number of drawbacks. Some bending sections are—in particular due to the materials or production methods used—not suitable for single-use endoscopes. Further, the annular or tubular bending segments forming the bending section are often not suitably kept together and do not feature a sufficient torsional/rotational stiffness. In addition, bending sections formed by separate annular or tubular bending segments as known in the related art often also provide limited design freedom. Sometimes it is difficult to provide a very small outer diameter of the insertion cord on the one hand and to provide a relatively large-diameter working channel inside the insertion cord on the other hand.

On this background, it is desirable to provide an endoscope which at least mitigates some of the above-mentioned drawbacks.

SUMMARY

The tasks and objectives of the present disclosure are to eliminate or at least to reduce the disadvantages of the related art. In particular, an endoscope shall be provided which is designed for single-use, which has a bending section having a suitable rotational/torsional stiffness and comprising bending segments, which are suitably kept together. Further, it would be desirable to provide a bending section enabling design freedom inside the bending section and enabling a reduction of the outer diameter of the insertion cord and/or a relative enlargement of a working channel arranged inside the insertion cord.

In a first aspect of the invention, an endoscope is provided that includes a bending section comprising segments including intermediate segments being separate annular or tubular segments, the intermediate segments comprising first intermediate segments and second intermediate segments arranged alternately one after the other in a proximal-distal direction, with hinges between the first intermediate segments and the second intermediate segments formed by hinge protrusions engaging in hinge recesses, and with steering wire portions running on the inner lumen of the first intermediate segments and on axially extending grooves of the second intermediate segments, and where stabilizing protrusions of the first intermediate segments are accommodated in the axially extending grooves of the second intermediate segments.

In a second aspect of the invention, a visualization system is provided, the visualization system including an endoscope according to the first aspect and a monitor communicatively coupled thereto.

In a third aspect of the invention, a method of making the endoscope according to the first aspect is provided. The method includes stacking the first intermediate segments and the second intermediate segments alternately one after the other in a proximal-distal direction, and threading the steering wire portions through the inner lumens of the first intermediate segments and on the axially extending grooves of the second intermediate segments.

In an embodiment according to the first aspect an endoscope comprises: an handle or interface; and an insertion cord configured to be inserted into a patient's body cavity and comprising an actively bendable bending section, the bending section comprising a plurality of bending segments including a proximal end segment, a plurality of intermediate segments and a distal end segment, the plurality of intermediate segments being separate annular or tubular segments made from a polymer material and having an outer circumferential side or surface and an inner circumferential side or surface, the plurality of intermediate segments comprising a plurality of first intermediate segments and a plurality of second intermediate segments being arranged alternately one after the other in a proximal-distal direction, wherein hinges between the first intermediate segments and the second intermediate segments are formed by hinge protrusions engaging in hinge recesses, wherein steering wires run on the inner circumferential side or surface of the first intermediate segments and on the outer circumferential side or surface in axially extending grooves of the second intermediate segments and keep the alternately arranged first intermediate segments and second intermediate segments together, and wherein the first intermediate segments comprise stabilizing protrusions arranged and accommodated in the axially extending grooves of the second intermediate segments, in which the steering wires run.

The endoscope according to the first aspect is preferably a low-cost, lightweight, single-use endoscope, which is intended to be disposed after use. This means that the endoscope is preferably optimized for one single use. The endoscope preferably has a limited number of elements, which are preferably manufactured with a low-cost material (polymer/plastic/resin) in preferably a low-cost manufacturing process (plastic/injection molding) and which can be easily assembled. Compared to traditional reusable endoscopes, the focus of the present disclosure is to provide an endoscope which is only used once and which thus does not have to withstand rather aggressive cleaning or sterilization processes and general harsh handling over the life cycle of the endoscope.

Preferably, the insertion cord of the endoscope is connected to the handle or interface and comprises an insertion tube, the actively bendable bending section and a distal tip unit extending in this order in the proximal-distal direction. The proximal end segment of the bending section is the proximal-most bending segment of the plurality of bending segments and is preferably adapted to be connected to the insertion tube of the insertion cord. The distal end segment of the bending section is the distal-most bending segment of the plurality of bending segments and is preferably adapted to be connected to the distal tip unit of the insertion cord. Said differently, the proximal end segment and the distal end segment are preferably designed/adapted such that they may be suitably connected to a remainder of the insertion cord and thus provide suitable interface parts fitting to the remainder of the insertion cord.

The plurality of intermediate segments may be described as independent and separate annular or tubular/hollow cylindrical segments/parts. The intermediate segments being separate segments means that each intermediate segment is a separate and independent part and is not integrally (in one piece/material) connected with an adjacent bending segment e.g. via foil hinges/bendable bridges of material. The bending section according to the present disclosure thus preferably does not comprise a one piece or two-piece bending section body, but comprises a number of separate segments. Advantageously, this provides more freedom in the polymer material used since it is not necessary anymore to use a polymer material suitable for foil hinges/bendable bridges of material.

The intermediate segments may be made from a polymer/plastic material, preferably a thermoplastic material, according to the present disclosure. The proximal end segment and the distal end segment are preferably also made from a polymer/plastic material. The intermediate segments are preferably molded segments, in particular injection-molded segments. I.e. each intermediate segment is preferably a low-cost molded polymer part, which can be easily manufactured e.g. via injection-molding. The intermediate segments may alternatively also be manufactured via 3D printing of polymer/plastic material.

According to the present disclosure, two types of intermediate segments are provided, namely the first intermediate segments or intermediate segments A, which are intermediate segments according to a first type having a first design, and the second intermediate segments or intermediate segments B, which are intermediate segments according to a second type having a second design. The plurality of first intermediate segments and the plurality of second intermediate segments being arranged alternately one after the other in a proximal-distal direction means that in an axial/longitudinal direction of the bending section, no intermediate segment is connected to an intermediate segment being of the same type. I.e. no first intermediate segment is connected to another first intermediate segment and no second intermediate segment is connected to another second intermediate segment.

E.g., the first intermediate segment or segment A may be connected to the proximal end segment, and the second intermediate segment or segment B may be distally connected to the segment A, another segment A may be distally connected to the segment B, another segment B may be distally connected to said another segment A and so on, so that the following design is obtained: proximal end segment-segment A-segment B-segment A-segment B and so on. Alternatively, e.g. the second intermediate segment or segment B may be connected to the proximal end segment, and the first intermediate segment or segment A may be distally connected to the segment B, another segment B may be distally connected to the segment A, another segment A may be distally connected to said another segment B and so on, so that the following design is obtained: proximal end segment-segment B-segment A-segment B-segment A and so on. The distal end segment may be either connected to the first intermediate segment/segment A or to the second intermediate segment/segment B.

According to the present disclosure, hinges between the first intermediate segments and the second intermediate segments are formed by hinge protrusions engaging in hinge recesses. It may e.g. be provided that all intermediate segments, i.e. both the first intermediate segments and the second intermediate segments have both hinge protrusions and hinge recesses. Alternatively, it may be provided that the first intermediate segments/segments A have only hinge protrusions however no hinge recesses and the second intermediate segments/segments B have only hinge recesses however no hinge protrusions. Further alternatively, it may be provided that the second intermediate segments/segments B have only hinge protrusions however no hinge recesses and the first intermediate segments/segments A have only hinge recesses however no hinge protrusions.

The alternately arranged intermediate segments are kept together according to the present disclosure by steering wires running alternately on the outer circumferential side or surface and on the inner circumferential side or surface of the intermediate segments. The steering wires pass on the internal side, i.e. run on the inner circumferential side or surface of the first intermediate segments/segments A. I.e. the steering wires run radially inside with reference to a wall of the annular/tubular first intermediate segments/segments A over the entire axial length of the first intermediate segments/segments A. The steering wires pass on the external side, i.e. run on the outer circumferential side or surface of the second intermediate segments or segments B. I.e. the steering wires run radially outside with reference to a wall of the annular/tubular second intermediate segments/segments B. The intermediate segments are thus easily and reliably kept together according to the present disclosure by alternately arranging the steering wires radially inward with respect to the wall of the first intermediate segments over an entire axial length of the first intermediate segments and radially outward with respect to the wall of the second intermediate segments over an entire axial length of the second intermediate segments.

The steering wires/wire portions run in axially extending grooves in the second intermediate segments/segments B. The axially extending grooves may extend over the entire axial length of the second intermediate segments/segments B or may extend only over a portion of the axial length of the second intermediate segments/segments B. Seen in a cross-sectional view of the second intermediate segment the axially extending grooves are preferably formed by interrupting an essentially round/circular outer contour of the second intermediate segment by an essentially U-shaped/C-shaped/semicircular shaped recess, having in particular two essentially parallel leg portions connected by a rounded portion. Preferably, said recess in the outer circumferential side or surface leads to a projection protruding inwardly on the inner circumferential side or surface. A wall thickness of the second intermediate segments/segments B is preferably held approximately constant over the entire circumference. The axially extending groove may thus also be described as a gutter/trough/hollow, interrupting the tubular/cylindrical shape of the second intermediate segments and projecting radially inwardly.

Further, according to the present disclosure, the first intermediate segments or segments A comprise stabilizing protrusions, which are arranged and accommodated in the axially extending grooves provided in the second intermediate segments or segments B. I.e. according to the present disclosure the axially extending grooves provided in the second intermediate segments are formed/designed such that they accommodate both steering wires and stabilizing protrusions of the first intermediate segments. The stabilizing protrusions are preferably adapted in size and shape to the axially extending grooves such that a sufficient rotational/torsional stiffness is provided between adjacent intermediate segments. Said differently, the stabilizing protrusions of the first intermediate segments fit into the grooves of the second intermediate segments, which improves the rotational/torsional stiffness of the assembled bending section. In other words, the stabilizing protrusions preferably slide in the axially extending grooves provided for the steering wires/wire portions and lock a rotation (around a longitudinal axis of the insertion cord) between adjacent intermediate segments.

The rounded portion of the U-shaped recess is preferably configured to accommodate the respective steering wire running in the respective axially extending groove and the two parallel leg portions are distanced and adapted to the respective stabilizing protrusion of the first intermediate segment such that the two parallel leg portions form guide portions arranged in close proximity to and axially guiding the respective stabilizing protrusion.

Preferably, the first intermediate segments and the second intermediate segments are adapted to each other such that, when joining the first intermediate segments and the second intermediate segments together alternately, the hinges and passages for the steering wires are formed and the stabilizing protrusions of the first intermediate segments are inserted and guided into the axially extending grooves of the second intermediate segments. Advantageously the steering wires keep the intermediate segments together. Therefore, it is not necessary to provide, in particular mold, dedicated lumens for the steering wires, since the steering wire passages are preferably created during assembly of the two types of intermediate segments. This is particularly advantageous for small endoscopes, since there is more space available inside, i.e. in the inner lumen of the bending section of the endoscope, in case no dedicated lumens for steering wires delimited by walls having sufficient wall thicknesses have to be molded.

The stabilizing protrusions may have at least one tapered or rounded surface preventing, when the bending section is bent, an engagement of the stabilizing protrusions with the radially further inward steering wires and/or a lateral or radially outward protruding of the stabilizing protrusions. In particular, when the bending section is bent, the stabilizing protrusions either move radially inward or outward depending on the direction in which the bending section is bent. Depending on the size and shape of the axially extending grooves and on the bending angle between adjacent bending segments this may lead to a contact/engagement of the stabilizing protrusions with the steering wires running in the axially extending grooves. By providing a radially inner tapered or rounded surface, it is possible to provide compact axially extending grooves and to prevent contact/engagement of the stabilizing protrusions with the steering wires when two adjacent bending segments are bent. Further, depending on the bending angle and bending direction between adjacent bending segments the stabilizing protrusions may protrude radially outward/laterally when adjacent bending segments are bent which may lead to an increase of the effective outer diameter of the bending section in portions by the stabilizing protrusions, which may impede an insertion of the insertion cord into the patient's body cavity. By providing a radially outer tapered or rounded surface, it is possible to prevent the stabilizing protrusions from projecting radially outward. Therefore, according to a preferred embodiment two tapered or rounded surfaces may be provided. In some cases however, it may be acceptable if the stabilizing protrusions protrude radially outward/laterally and thus lose the interface in the grooves, in particular in case enough space is available inside the respective body cavity of the patient. In this case the bending section will still have a suitable rotational/torsional stiffness, since there will preferably still be opposite stabilizing protrusions arranged in the axially extending grooves, thereby still providing a 3-point-connection formed by two hinges and one (opposite) stabilizing protrusion.

The endoscope according to the present disclosure may be a one-plane bending endoscope configured to bend in two opposite directions (e.g. up-down). Alternatively, the endoscope may be a two-plane bending endoscope configured to bend in four directions (e.g. up-down and left-right).

The endoscope according to the present disclosure is preferably a small-diameter endoscope, in particular a bronchoscope, a ureteroscope or a cholangioscope (used as a baby endoscope in combination with a duodenoscope), etc. However, the present disclosure is neither limited to the endoscope being any one of the mentioned specific small-diameter endoscopes nor limited to the endoscope being a small-diameter endoscope. Said differently, the endoscope according to the present disclosure may advantageously be a duodenoscope, bronchoscope, arthroscope, colonoscope, laparoscope, gastroscope, etc.

In case the endoscope is a small outer diameter one-plane bending endoscope, the outer diameter of the insertion cord/the bending section is preferably less than 3 mm. In such a case, a working channel tube having an inner diameter of 1.1 mm to 1.3 mm may fit into an inner lumen of the bending section. In case the endoscope is a small outer diameter two-plane bending endoscope, the outer diameter of the insertion cord/the bending section is preferably less than 5 mm, e.g. around 4 mm to 4.5 mm. Obviously, the present disclosure is not limited to the endoscope having an outer diameter in the mentioned ranges. I.e. the outer diameter may of course be bigger.

In case the endoscope is a one-plane bending endoscope, it may be provided that each first intermediate segment comprises two hinge protrusions, two hinge recesses and four stabilizing protrusions and each second intermediate segment comprises two hinge protrusions, two hinge recesses and two axially extending grooves.

E.g., a first axial end of the first intermediate segment may comprise two hinge protrusions and two stabilizing protrusions and a second axial end of the first intermediate segment may comprise two hinge recesses and two stabilizing protrusions. A first axial end of the second intermediate segment may comprise two hinge protrusions and a second axial end of the second intermediate segment may comprise two hinge recesses. The two axially extending grooves may extend from the first axial end to the second axial end of the second intermediate segment.

The first intermediate segment and the second intermediate segment may be assembled by stacking/putting the first axial end of the second intermediate segment onto the second axial end of the first intermediate segment or by stacking/putting the first axial end of the first intermediate segment onto the second axial end of the second intermediate segment. An automatic assembly is conceivable.

The two hinge protrusions provided on the first axial end of the first intermediate segment are preferably arranged diametrically opposed with respect to a center axis of the first intermediate segment. The two stabilizing protrusions provided on the first axial end of the first intermediate segment are preferably arranged diametrically opposed with respect to a center axis of the first intermediate segment. A plane in which the two hinge protrusions on the first axial end lie is preferably perpendicular to a plane in which the two stabilizing protrusions on the first axial end lie. I.e. preferably the four protrusions (two hinge protrusions and two stabilizing protrusions) on the first axial end are equally spaced by 90° in the circumferential direction.

The two hinge recesses provided on the second axial end of the first intermediate segment are preferably arranged diametrically opposed with respect to a center axis of the first intermediate segment. The two stabilizing protrusions provided on the second axial end of the first intermediate segment are preferably arranged diametrically opposed with respect to a center axis of the first intermediate segment.

The two hinge recesses provided on the second axial end of the first intermediate segment are preferably axially aligned with the two hinge protrusions provided on the first axial end of the first intermediate segment. The two stabilizing protrusions provided on the second axial end of the first intermediate segment are preferably axially aligned with the two stabilizing protrusions provided on the first axial end of the first intermediate segment. I.e. a plane in which the two hinge recesses on the second axial end of the first intermediate segment lie is preferably perpendicular to a plane in which the two stabilizing protrusions on the second axial end of the first intermediate segment lie. Therefore, each hinge recess is spaced by 90° in the circumferential direction from two adjacent stabilizing protrusions.

The two hinge protrusions provided on the first axial end of the second intermediate segment are preferably arranged diametrically opposed with respect to a center axis of the second intermediate segment. The two hinge recesses provided on the second axial end of the second intermediate segment are preferably arranged diametrically opposed with respect to a center axis of the second intermediate segment. Preferably, the two hinge protrusions are axially aligned with the two hinge recesses, i.e. a plane may be defined in which the two hinge protrusions and the two hinge recesses lie. The two axially extending grooves are preferably spaced by 90° in the circumferential direction from adjacent hinge protrusions/recesses.

It preferably applies that for both segment types, i.e. for the first intermediate segment and the second intermediate segment, a hinge plane can be defined in which both segment types are provided with two hinge protrusions in one (axial) end with reference to a proximal-distal direction and with two hinge recesses or notches in the other, i.e. opposite, (axial) end with reference to the proximal-distal direction. The hinge protrusions are preferably adapted/configured to engage with the hinge recesses/notches to form hinges.

In case the endoscope is a two-plane bending endoscope, it may be provided that each first intermediate segment comprises four hinge protrusions and four stabilizing protrusions and each second intermediate segment comprises four hinge recesses and four axially extending grooves.

E.g. a first axial end of the first intermediate segment may comprise two hinge protrusions and two stabilizing protrusions and a second axial end of the first intermediate segment may comprise two hinge protrusions and two stabilizing protrusions. A first axial end of the second intermediate segment may comprise two axially extending grooves and two hinge recesses and a second axial end of the second intermediate segment may comprises two axially extending grooves and two hinge recesses.

The first intermediate segment and the second intermediate segment may be assembled by stacking/putting the first axial end of the second intermediate segment onto the second axial end of the first intermediate segment or by stacking/putting the first axial end of the first intermediate segment onto the second axial end of the second intermediate segment. An automatic assembly is conceivable.

The two hinge protrusions provided on the first axial end of the first intermediate segment are preferably arranged diametrically opposed with respect to a center axis of the first intermediate segment. The two stabilizing protrusions provided on the first axial end of the first intermediate segment are preferably arranged diametrically opposed with respect to a center axis of the first intermediate segment. A plane in which the two hinge protrusions on the first axial end lie is preferably perpendicular to a plane in which the two stabilizing protrusions on the first axial end lie. I.e. preferably the four protrusions (two hinge protrusions and two stabilizing protrusions) on the first axial end are spaced by 90° in the circumferential direction, respectively.

The two hinge protrusions provided on the second axial end of the first intermediate segment are preferably arranged diametrically opposed with respect to a center axis of the first intermediate segment. The two stabilizing protrusions provided on the second axial end of the first intermediate segment are preferably arranged diametrically opposed with respect to a center axis of the first intermediate segment. The two hinge protrusions provided on the second axial end of the first intermediate segment are preferably axially aligned with the two stabilizing protrusions provided on the first axial end of the first intermediate segment. The two stabilizing protrusions provided on the second axial end of the first intermediate segment are preferably axially aligned with the two hinge protrusions provided on the first axial end of the first intermediate segment. Preferably, the four protrusions (two hinge protrusions and two stabilizing protrusions) on the second axial end are spaced by 90° in the circumferential direction, respectively.

The two hinge recesses provided on the first axial end of the second intermediate segment are preferably arranged diametrically opposed with respect to a center axis of the second intermediate segment. The two axially extending grooves provided on the first axial end of the second intermediate segment are preferably arranged diametrically opposed with respect to a center axis of the second intermediate segment. A plane in which the two hinge recesses on the first axial end lie is preferably perpendicular to a plane in which the two axially extending grooves on the first axial end lie. I.e. preferably the four recesses/grooves on the first axial end are spaced by 90° in the circumferential direction, respectively.

The two hinge recesses provided on the second axial end of the second intermediate segment are preferably arranged diametrically opposed with respect to a center axis of the first intermediate segment. The two axially extending grooves provided on the second axial end of the second intermediate segment are preferably arranged diametrically opposed with respect to a center axis of the second intermediate segment. The two hinge recesses provided on the second axial end of the second intermediate segment are preferably axially aligned with the two axially extending grooves provided on the first axial end of the second intermediate segment. The two axially extending grooves provided on the second axial end of the second intermediate segment are preferably axially aligned with the two hinge recesses provided on the first axial end of the second intermediate segment. Preferably, the four recesses/axially extending grooves on the second axial end are spaced by 90° in the circumferential direction, respectively.

It preferably applies that when assembling a first intermediate segment and a second intermediate segment, the hinge protrusions are received in hinge recesses and the stabilizing protrusions are received in the axially extending grooves.

According to a preferred embodiment (relating in particular to both one-plane and two-plane bending endoscopes) an angle or a gap between adjacent segments of the plurality of intermediate segments may be varied along the proximal-distal direction for providing different bending angles at different positions in the proximal-distal direction.

In particular the first intermediate segments/segments A and the second intermediate segments/segments B may be designed such that an angle or gap between two segments A and B defines a maximum bending angle of the hinge between the two segments A and B. The angle or gap may be varied along the proximal-distal direction in order to provide different bending angles at different positions in the proximal-distal direction. Advantageously, a preselected specific bending shape of the bending section may be achieved, e.g. a specific bending angle as a function of the length from a proximal end of the bending section may be defined. It may thus be possible to preselect the shape of the fully bent bending section and to provide different angles at different positions in the proximal-distal direction.

Preferably, at least one of the plurality of intermediate segments comprises an inner bulged portion keeping cables and/or tubes arranged in an inner lumen of the at least one of the plurality of intermediate segments in place during bending of the bending section. E.g., inner bulges may be provided in the first intermediate segments and/or the second intermediate segments to keep cables/tubes etc. provided inside the inner lumen in place. Bulges may be formed integral with the intermediate segments to keep electrical cables in place during bending. These bulges or bulged portions may be assisted by the axially extending grooves protruding radially inwardly and a working channel tube arranged in the inner lumen of the bending section in keeping the respective cables and/or tubes in place.

According to the present disclosure, by providing individual/separate intermediate bending segments made of a polymer material, a low-cost and lightweight bending section suitable for a single-use endoscope is provided. By alternately arranging the steering wires on the inner circumferential side of the first intermediate segments and on the outer circumferential side of the second intermediate segments, the individual/separate intermediate bending segments are suitably held and kept together. This is in particular made possible by providing the axially extending grooves in the second intermediate segments. The axially extending grooves additionally serve to accommodate stabilizing protrusions according to the present disclosure, so that the bending section assembled/formed by the plurality of individual segments receives a suitable rotational/torsional stiffness. Further, the axially extending grooves make it possible that no inner lumens/passages are necessary. Therefore, the available inner space can be suitably used, enabling a design freedom and making it possible e.g. to provide a relative bigger working channel tube inside the bending section for a given outer diameter of the insertion cord.

In the present disclosure "proximal" means "in a direction away from a patient towards a user" and "distal" means "in a direction towards the patient away from the user".

BRIEF DESCRIPTION OF THE DRAWINGS

The foregoing embodiments, variations, and examples thereof will now be described in greater detail with reference to non-limiting examples illustrated in the appended drawings, of which.

The figures are schematic in nature and serve only to understand the disclosure. Identical elements are marked with the same reference signs. The features of the different embodiments can be interchanged among each other.

DETAILED DESCRIPTION

Figure 1:
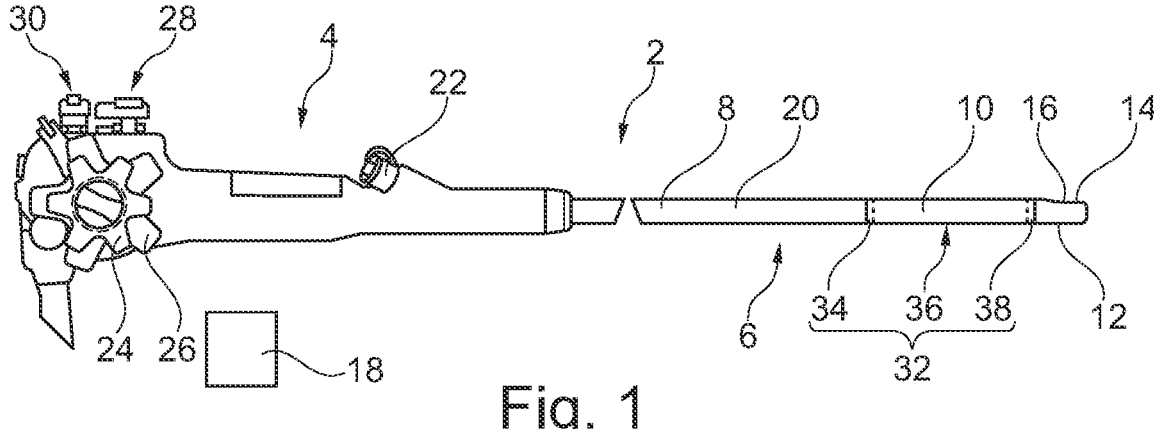
FIG. 1 is a side view showing a two-plane bending endoscope according to a first embodiment of the present disclosure.

In FIG. 1, an endoscope 2 according to the first aspect of the invention is shown. The endoscope includes a bending section comprising segments including intermediate segments being separate annular or tubular segments, the intermediate segments comprising first intermediate segments and second intermediate segments arranged alternately one after the other in a proximal-distal direction, with hinges between the first intermediate segments and the second intermediate segments formed by hinge protrusions engaging in hinge recesses, and with steering wire portions running on the inner lumen of the first intermediate segments and on axially extending outer grooves of the second intermediate segments. Stabilizing protrusions of the first intermediate segments are accommodated in the axially extending outer grooves of the second intermediate segments.

The provision of hinge and stabilizing protrusions engaged in grooves and recesses, with intermediate segments of the first and second types staggered enables the manufacture of smaller diameter endoscopes, relative to known endoscopes for similar procedures, with proper flexibility and torsional rigidity and with enough space internally to include working channel tubes and other tubes.

Single-use endoscopes optimize workflow and reduce cost while saving patient's lives and improving patient care. They optimize workflow and reduce cost because they are always ready when needed without the traditional large-scale capital and repair budgets required for reusable endoscopes. For example, a sterilization and storage facility is avoided, there is no need to maintain evidence of sterilization, and there is no need to transport endoscopes from sterilization and storage facilities to the buildings where they are needed, sometimes in the middle of the night or weekends. They save patient's lives and improve patient care because they are readily available and do not pose a cross-contamination risk. This also reduces hospital re-admissions. While single-use endoscopes are disposed after a single patient use (one or more procedures may be performed while the patient remains in the treatment room), the environmental impact of re-useable endoscopes, due to cleaning materials, $CO_2$ emissions during the cleaning process, and use of disposable personal protective equipment by personnel involved in transportation and sterilization of the re-useable endoscopes, is similar to that of single-use endoscopes. Studies are emerging showing that the environmental impact of single-use endoscopes may, in fact, be less than that of re-usable endoscopes. To further reduce environmental impact, the endoscopes according to the present disclosure are primarily made of polymer materials. Non-polymer materials are typically used for the steering wires, insertion tube or shaft, and electronics components, such as the camera(s), light emitting diodes, circuit boards and components connected to the circuit boards. Endoscopes with elevator bars may include a metal elevator bar wire. The distal tip part may be made, except for the electronic components and wires, exclusively of polymer materials. As the focus on reducing environmental impact continues, for example by using polymeric wires as described in commonly owned U.S. Pat. No. 11,291,355, issued on Apr. 5, 2022, the environmental impact of single-use endoscopes will likely continue to shrink.

Figure 17:
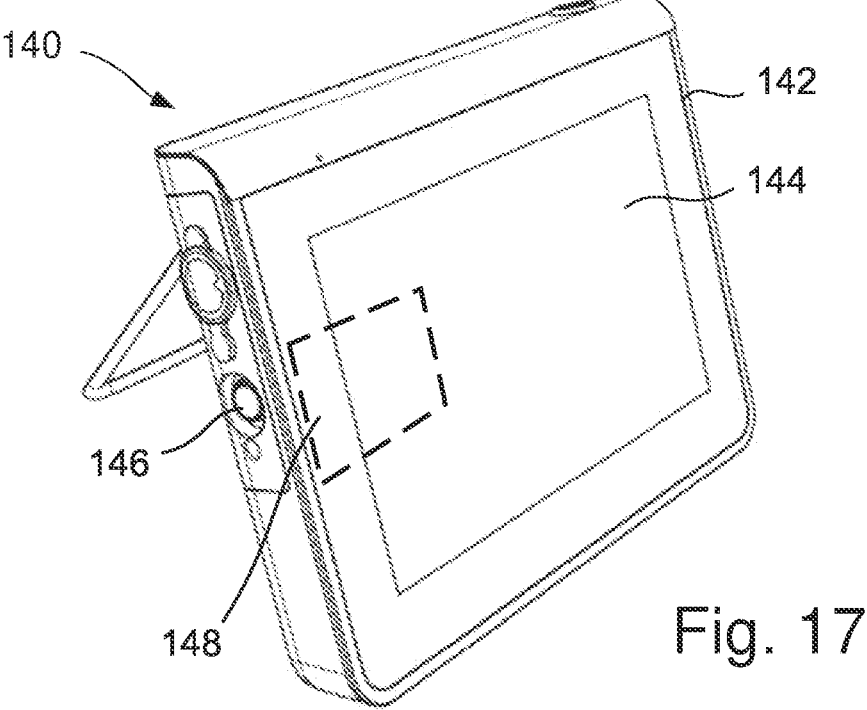
FIG. 17 is a perspective view of a monitor connectable to the endoscope according to the present disclosure.
Figure 18:
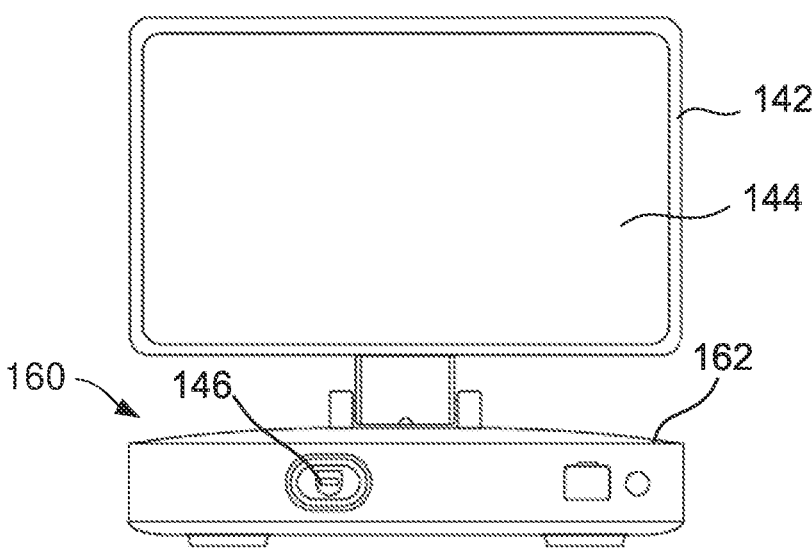
FIG. 18 is a front view of a monitor connectable to the endoscope according to the present disclosure.

In a first embodiment according to the first aspect, the endoscope 2 is preferably a single-use endoscope. The endoscope 2 comprises a proximal handle 4 designed to be held by a user and being configured to accommodate operating parts of the endoscope 2. The endoscope 2 further comprises an insertion cord 6 configured to be inserted into a patient's body cavity. The insertion cord 6 comprises an insertion tube 8, a bending section 10 and a distal tip unit 12, which extend in this order from the handle 4. In the distal tip unit 12 a light emitting device 14 and an imaging device 16 are accommodated, so that the patient's body cavity can be illuminated and inspected. Pictures/videos captured by the imaging device 16 can be shown on a monitor 18. Variations of the monitor 18, denoted by numerals 140 and 160, are illustrated in FIGS. 17 and 18. These monitors are provided separately from, and are connectable with, the endoscope 2 via a cable or wirelessly.

The endoscope 2 has an internal working channel 20, which is accessible via an access port 22 and via which a surgical tool or instrument can be guided into the patient's body cavity.

The handle 4 comprises two steering wheels, namely a first steering wheel 24 and a second steering wheel 26, which are arranged coaxially and which can be rotated by the user in order to bend the bending section 10 for steering the distal tip unit 12. In particular, one of the steering wheels 24, 26, e.g. the first steering wheel 24, can be operated by the user to bend the bending section 10 in a first bending plane (e.g. in an up-and-down direction) and the other one of the steering wheels 24, 26, e.g. the second steering wheel 26, can be operated by the user to bend the bending section 10 in a second bending plane (e.g. in a right-and-left direction). The first bending plane is preferably perpendicular to the second bending plane. The endoscope 2 shown in FIG. 1 is thus a two-plane bending endoscope.

The handle 4 further comprises two valves, namely a gas/water injection valve 28 and a suction valve 30. The gas/water injection valve 28 and the suction valve 30 are arranged side by side on a top surface of a housing of the handle 4.

The bending section 10 comprises a plurality of bending segments 32 including a proximal end segment 34, a plurality of intermediate segments 36 and a distal end segment 38. The proximal end segment 34 is connected to the insertion tube 8. The distal end segment 38 is connected to the distal tip unit 12. The plurality of intermediate segments 36 is arranged between the proximal end segment 34 and the distal end segment 38. The plurality of bending segments 32 may be made from a polymer material, in particular a thermoplastic material, and are molded, especially injection-molded, parts.

A positioning interface, or interface, functions to control the position of the insertion cord 6. The handle 4 is an example of a positioning interface and, unless stated otherwise, the terms are used interchangeably. The positioning interface also functions to provide the steering controls, e.g. knobs, levers, buttons, and the like, used to steer the tip of the insertion cord 6, which includes the camera, and the elevator controls. Alternatively, a different positioning interface can be provided that is connected to the insertion cord and is detachably connected to a robotic arm. In a further alternative, the positioning interface is detachably connected to the insertion cord and is therefore reusable. In this example the positioning interface may be affixed to a robotic arm. The insertion cord thus extends from the robotic arm, and the intrusive medical device is detachable from the robotic arm. The robotic arm responds to signals, including voice commands from an operator, to rotate, translate, and otherwise position the proximal end of the insertion cord, as an operator would do manually. The positioning interface can include control actuators, including manual control actuators. Alternatively or additionally, control actuators can be provided in or on the robotic arm or by the robotic system including the robotic arm, thereby potentially reducing the cost of the intrusive medical device. Example control actuators include single axis actuators, including linear motion actuators. A linear motion actuator may comprise a threaded rod coupled to a threaded nut portion, in which a motor rotates the rod to translate the nut portion.

Figure 2:
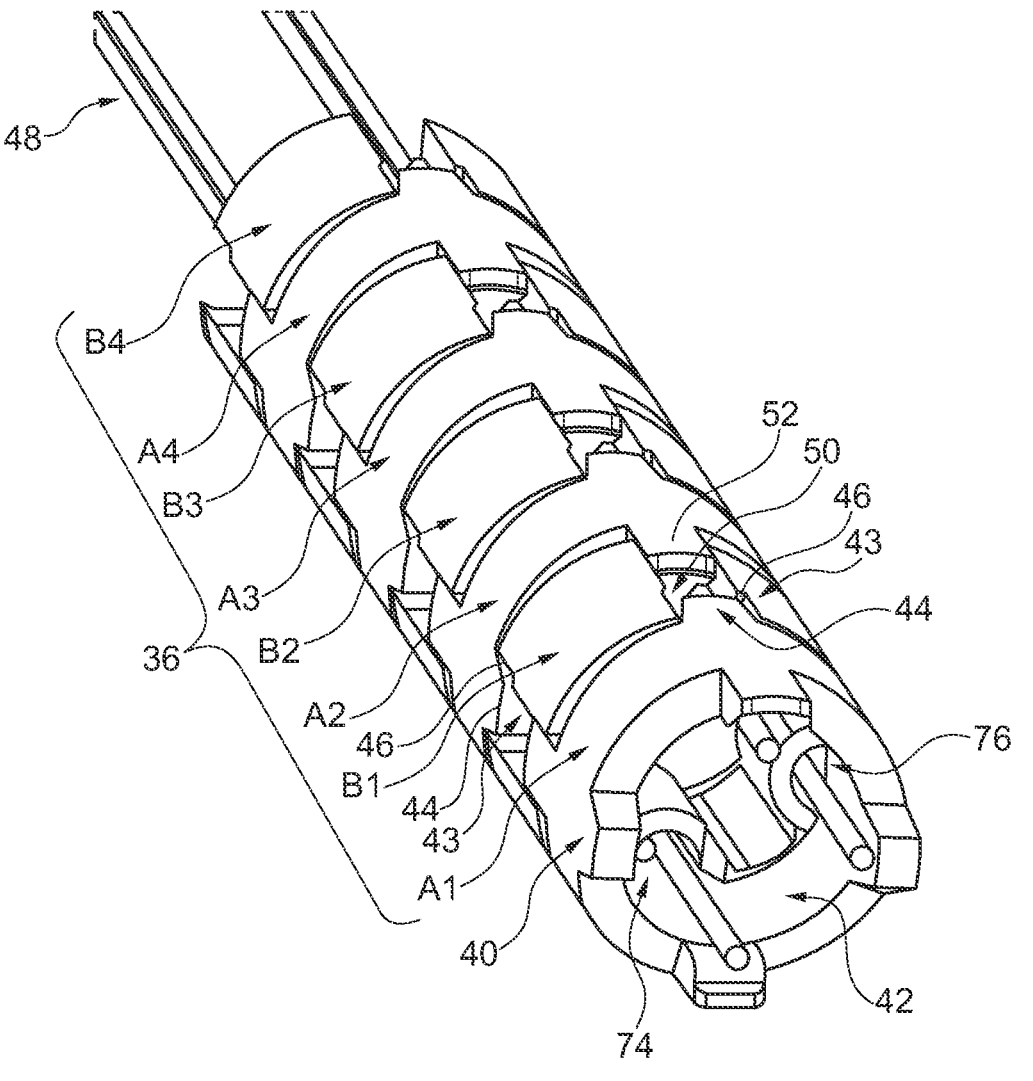
FIG. 2 is a perspective view of intermediate bending segments comprising first intermediate segments and second intermediate segments arranged alternately one after the other according to the first embodiment.

As can be seen in FIG. 2 the plurality of intermediate segments 36 are separate annular or tubular segments and have an outer circumferential side or surface 40 and an inner circumferential side or surface 42. The plurality of intermediate segments 36 comprise first intermediate segments A1, A2, A3, A4 and second intermediate segments B1, B2, B3, B4, which are arranged alternately one after the other in a proximal-distal direction. I.e. the first intermediate segment A1 is connected to the second intermediate segment B1, the second intermediate segment B1 is connected to the first intermediate segment A2, the first intermediate segment A2 is connected to the second intermediate segment B2 and so on. The first intermediate segment A1 may be connected to the distal end segment 38 and the second intermediate segment B4 may be connected to the proximal end segment 34. However, there may alternatively be provided more or less intermediate segments 36.

Hinges 43 between the first intermediate segments A (A1, A2, A3, A4) and the second intermediate segments B (B1, B2, B3, B4) are formed by hinge protrusions 44 engaging in hinge recesses 46. The hinge 43 between the first intermediate segment A1 and the second intermediate segment B1 enables a left-right bending between the adjacent intermediate segments A1, B1. The hinge 43 between the second intermediate segment B1 and the first intermediate segment A2 enables an up-down bending between the adjacent intermediate segments B1, A2. Left-right bending is further enabled by the hinges 43 between adjacent intermediate segments A2, B2, between adjacent intermediate segments A3, B3 and between adjacent intermediate segments A4, B4.

Up-down bending is further enabled by the hinges 43 between adjacent intermediate segments B2, A3 and between adjacent intermediate segments B3, A4. The intermediate segments 36 shown in FIG. 2 thus enable two-plane bending of the bending section 10. The bending is effected by four steering wire portions 48, which are pulled and released by rotating the first steering wheel 24 and the second steering wheel 26.

Figures 3, 4, 5:
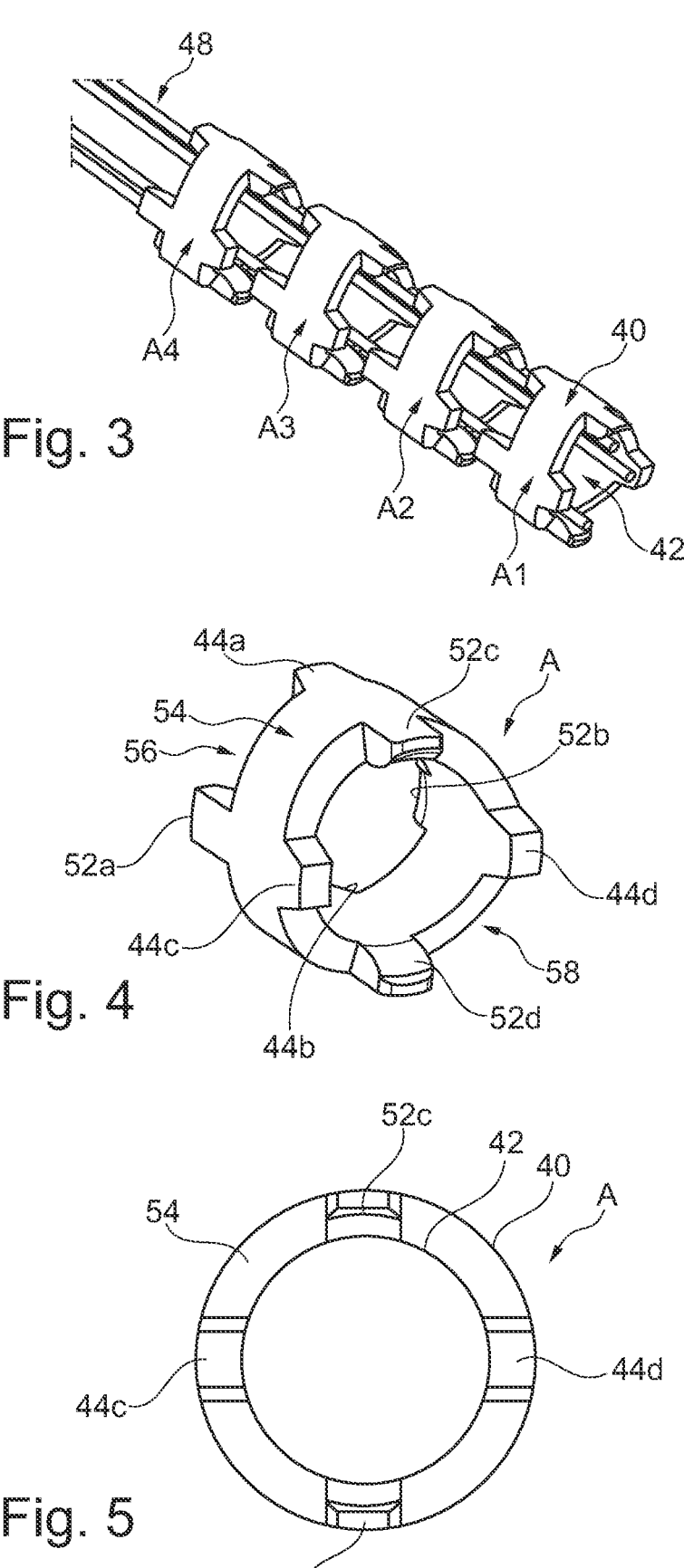
FIG. 3 is a perspective view showing only the first intermediate segments shown in FIG. 2, with the second intermediate segments removed for illustration purposes.
FIG. 4 is a perspective view of one first intermediate segment shown in FIG. 3.
FIG. 5 is a top view of the one first intermediate segment shown in FIG. 4.
Figures 6, 7, 8:
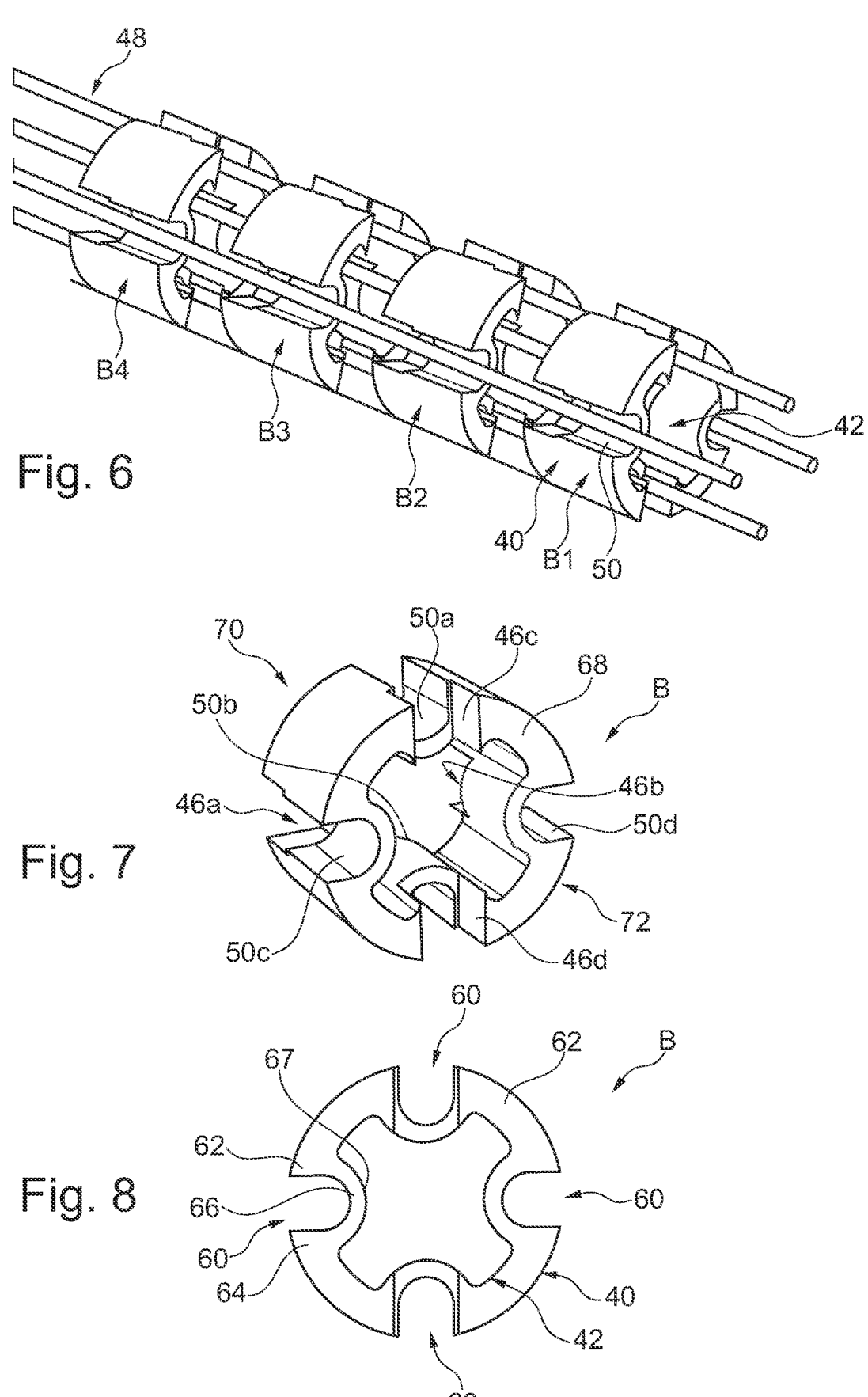
FIG. 6 is a perspective view showing only the second intermediate segments shown in FIG. 2, with the first intermediate segments removed for illustration purposes.
FIG. 7 is a perspective view of one second intermediate segment shown in FIG. 6.
FIG. 8 is a top view of the one second intermediate segment shown in FIG. 7.

The steering wire portions 48 run in the inner lumen on the inner circumferential side or surface 42 of the first intermediate segments A (A1, A2, A3, A4) and on the outer circumferential side or surface 40 in axially extending outer grooves 50 of the second intermediate segments B (B1, B2, B3, B4) and keep the alternately arranged first intermediate segments A and second intermediate segments B together. FIG. 3 in particular shows only the first intermediate segments A1, A2, A3 and A4, with the second intermediate segments B1, B2, B3 and B4 removed for illustration purposes. The steering wire portions 48 pass on the internal side, i.e. run radially inside with reference to a wall of the annular/tubular first intermediate segments A1, A2, A3 and A4 over the entire axial length of the first intermediate segments A1, A2, A3 and A4. FIG. 6 shows only the second intermediate segments B1, B2, B3 and B4, with the first intermediate segments A1, A2, A3 and A4 removed for illustration purposes. The steering wire portions 48 pass on the external side, i.e. run radially outside with reference to a wall of the annular/tubular second intermediate segments B1, B2, B3 and B4 over the entire axial length of the second intermediate segments B1, B2, B3 and B4. The axially extending grooves 50 extend over a portion of the axial length of the second intermediate segments B1, B2, B3 and B4. In the assembled state of the intermediate segments 36 shown in FIG. 2 stabilizing protrusions 52 are arranged and accommodated in the axially extending grooves 50, in which the steering wire portions 48 run.

FIG. 4 shows a perspective view of the first intermediate segment A and FIG. 5 is a top view of the first intermediate segment A. The first intermediate segment A has a tubular/hollow-cylindrical/annular body 54 having a circular outer circumferential side or surface 40 and a circular inner circumferential side or surface 42. The first intermediate segment A further has four hinge protrusions 44a, 44b, 44c, 44d and four stabilizing protrusions 52a, 52b, 52c, 52d, which extend axially away from the tubular body 54. The hinge protrusions 44a, 44b, 44c, 44d each have a shape of a trapezoid block portion when looking at the first intermediate segment A from a side, with the long basic side/surface connected to the tubular body 54, the hinge protrusions 44a, 44b, 44c, 44d thus having inclined surfaces towards the short basic side/surface. The stabilizing protrusions 52a, 52b, 52c, 52d each have a radially inner inclined or rounded surface leading to a decreasing wall thickness of the stabilizing protrusions 52a, 52b, 52c, 52d starting from the tubular body 54.

On a first axial end 56 of the tubular body 54 two hinge protrusions 44a, 44b and two stabilizing protrusions 52a, 52b extend axially away in a proximal direction, and on a second axial end 58 of the tubular body 54 two hinge protrusions 44c, 44d and two stabilizing protrusions 52c, 52d extend axially away in a distal direction. The two hinge protrusions 44a, 44b provided on the first axial end 56 of the first intermediate segment A are arranged diametrically opposed with respect to a center axis of the first intermediate segment A. The two stabilizing protrusions 52a, 52b provided on the first axial end 56 of the first intermediate segment A are arranged diametrically opposed with respect to the center axis of the first intermediate segment A. The four protrusions 44a, 44b, 52a, 52b on the first axial end 56 are equally spaced in the circumferential direction.

The two hinge protrusions 44c, 44d provided on the second axial end 58 of the first intermediate segment A are arranged diametrically opposed with respect to the center axis of the first intermediate segment A. The two stabilizing protrusions 52c, 52d provided on the second axial end 58 of the first intermediate segment A are arranged diametrically opposed with respect to the center axis of the first intermediate segment A. The two hinge protrusions 44c, 44d provided on the second axial end 58 of the first intermediate segment A are axially aligned with the two stabilizing protrusions 52a, 52b provided on the first axial end 56 of the first intermediate segment A. The two stabilizing protrusions 52c, 52d provided on the second axial end 58 of the first intermediate segment A are axially aligned with the two hinge protrusions 44a, 44b provided on the first axial end 56 of the first intermediate segment A. The four protrusions 44c, 44d, 52c, 52d on the second axial end 58 are equally spaced in the circumferential direction.

FIG. 7 shows a perspective view of the second intermediate segment B and FIG. 8 is a top view of the second intermediate segment B. An essentially circular outer contour/wall of the second intermediate segment B is interrupted by four U-shaped recesses 60, each having two parallel leg portion 62, 64 connected by a rounded portion 66. Said U-shaped recesses 60 on the outer circumferential side or surface 40 lead to projections 67 protruding radially inwardly on the inner circumferential side or surface 42. Therefore, an essentially circular inner contour/wall of the second intermediate segment B is interrupted by the four projections 67. Therefore, both the outer circumferential side or surface 40 and the inner circumferential side or surface 42 are non-circular. Each second intermediate segment B has a recessed body 68 comprising four hinge recesses 46a, 46b, 46c, 46d and four axially extending grooves 50a, 50b, 50c, 50d. A first axial end 70 of the second intermediate segment B comprises two hinge recesses 46a, 46b and two axially extending grooves 50a, 50b and a second axial end 72 of the second intermediate segment B comprises two hinge recesses 46c, 46d and two axially extending grooves 50c, 50d. The two hinge recesses 46a, 46b provided on the first axial end 70 of the second intermediate segment B are arranged diametrically opposed with respect to a center axis of the second intermediate segment B.

The two axially extending outer grooves 50a, 50b provided on the first axial end 70 of the second intermediate segment B are arranged diametrically opposed with respect to the center axis of the second intermediate segment B. The four recesses/grooves 46a, 46b, 50a, 50b on the first axial end 70 are equally spaced in the circumferential direction. The two hinge recesses 46c, 46d provided on the second axial end 72 of the second intermediate segment B are arranged diametrically opposed with respect to the center axis of the second intermediate segment B. The two axially extending grooves 50c, 50d provided on the second axial end 72 of the second intermediate segment B are arranged diametrically opposed with respect to the center axis of the second intermediate segment B. The two hinge recesses 46c, 46d provided on the second axial end 72 of the second intermediate segment B are axially aligned with the two axially extending grooves 50a, 50b provided on the first axial end 70 of the second intermediate segment B. The two axially extending grooves 50c, 50d provided on the second axial end 72 of the second intermediate segment B are axially aligned with the two hinge recesses 46a, 46b provided on the first axial end 70 of the second intermediate segment B. The four recesses/grooves on the second axial end 72 are equally spaced in the circumferential direction.

The intermediate segments 36 are assembled by stacking the first axial end 70 of the second intermediate segments B onto the second axial end 58 of the first intermediate segment A or by stacking the first axial end 56 of the first intermediate segment A onto the second axial end 72 of the second intermediate segment B. When assembling the plurality of first intermediate segments A1, A2, A3, A4 and the plurality of second intermediate segment 131, B2, B3, B4, the hinge protrusions 44 of the first intermediate segments A1, A2, A3, A4 are received in the hinge recesses 46 of the second intermediate segments 131, B2, B3, B4 and the stabilizing protrusions 52 of the first intermediate segments A1, A2, A3, A4 are received in the axially extending grooves of the second intermediate segments 131, B2, B3, B4. In the assembled state as shown in FIG. 2 one large inner lumen 74 and four steering wire passages 76 for the steering wire portions 48 are formed.

In a variation of the present embodiment, the hinge recesses are longitudinally adjacent the axially extending outer grooves. When the endoscope is a two-plane bending endoscope, each of the first intermediate segments include two of the hinge protrusions and two of the stabilizing protrusions extending distally from the body and two of the hinge protrusions and two of the stabilizing protrusions extending proximally from the body. The axially extending outer grooves include opposing surfaces and a bottom surface connecting the opposing surfaces and providing a groove bottom on which a portion of the steering wire is received. The recesses for the stabilizing protrusions include opposing surfaces without the bottom surface. The two of the hinge protrusions extending distally from the body are offset 90 degrees from the two of the hinge protrusions extending proximally from the body. The insertion cord may have an outer diameter of less than 5 mm.

As seen in FIG. 7, two of the axially extending outer grooves extend distally from a proximal surface and may be referred to as proximal grooves, and two of the axially extending outer grooves extend proximally from a distal surface of the second intermediate segments and may be referred to as distal grooves. Hinge recesses are positioned proximally of and aligned with the distal grooves; and the hinge recesses are positioned distally of and aligned with the proximal grooves. The distal grooves are offset radially and longitudinally from the proximal grooves.

In another variation of the present embodiment, the endoscope is a one-plane bending endoscope. Each of the first intermediate segments include two of the hinge protrusions and two of the stabilizing protrusions extending distally from the body and two of the hinge protrusions and two of the stabilizing protrusions extending proximally from the body. The axially extending outer grooves include opposing surfaces and a bottom surface connecting the opposing surfaces and providing a groove bottom on which a portion of the steering wire is received. The recesses for the stabilizing protrusions include opposing surfaces without the bottom surface. The two of the hinge protrusions extending distally from the body are longitudinally aligned with the two of the hinge protrusions extending proximally from the body. The insertion cord may have an outer diameter of less than 3 mm.

Figures 9, 10, 11:
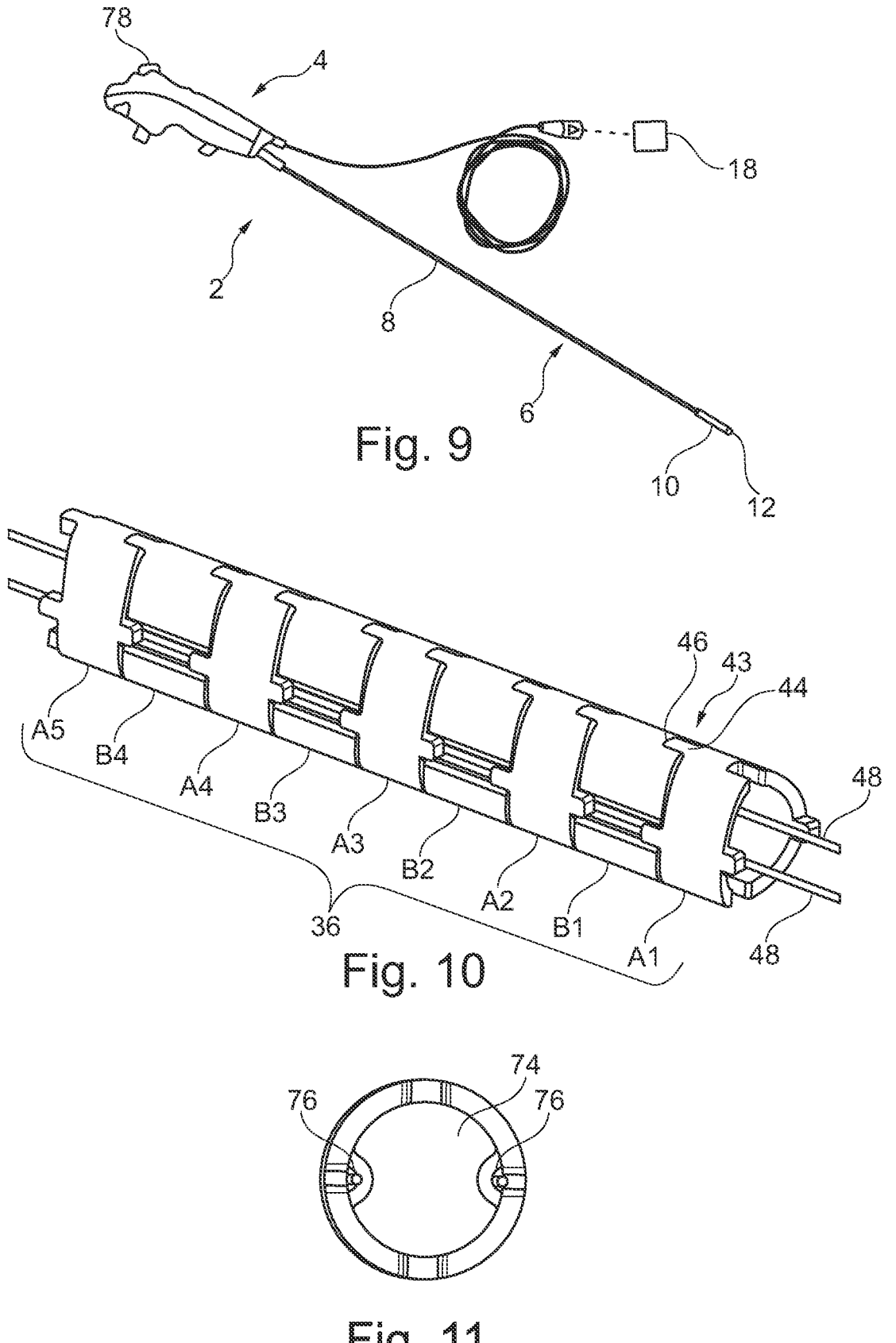
FIG. 9 is a perspective view showing a one-plane bending endoscope according to a second embodiment of the present disclosure.
FIG. 10 is a perspective view of intermediate bending segments comprising first intermediate segments and second intermediate segments arranged alternately one after the other according to the second embodiment.
FIG. 11 is a top view of the assembly of intermediate bending segments shown in FIG. 10.

FIG. 9 is a perspective view showing a one-plane bending endoscope 2 according to a second embodiment of the present disclosure. The endoscope 2, which is preferably also a single-use endoscope, comprises a proximal handle 4 and an insertion cord 6 comprising an insertion tube 8, a bending section 10 and a distal tip unit 12. The bending section 10 may be bent by operating a lever 78 provided at the handle 4. A monitor 18 illustrated in FIG. 17 is connected to the endoscope 2 via a cable or wirelessly.

FIG. 10 is a perspective view of intermediate segments 36 of the bending section 10, wherein the intermediate segments 36 comprise first intermediate segments A1, A2, A3, A4, A5 and second intermediate segments B1, B2, B3, B4 arranged alternately one after the other. Hinges 43 between the first intermediate segments A (A1, A2, A3, A4, A5) and the second intermediate segments B (B1, B2, B3, B4) are formed by hinge protrusions 44 engaging in hinge recesses 46. The hinges 43 only enable left-right bending. The bending is effected by two steering wire portions 48, which are pulled and released by operating the lever 78. The steering wire portions 48 can be two separate wires or two portions of a common wire joined at the distal end, as describe, for example, in commonly owned U.S. patent application Ser. No. 18/037,958, filed May 19, 2023, and in commonly owned U.S. Pat. No. 11,622,674, issued Apr. 11, 2023, which are incorporated herein by reference.

Figure 12:
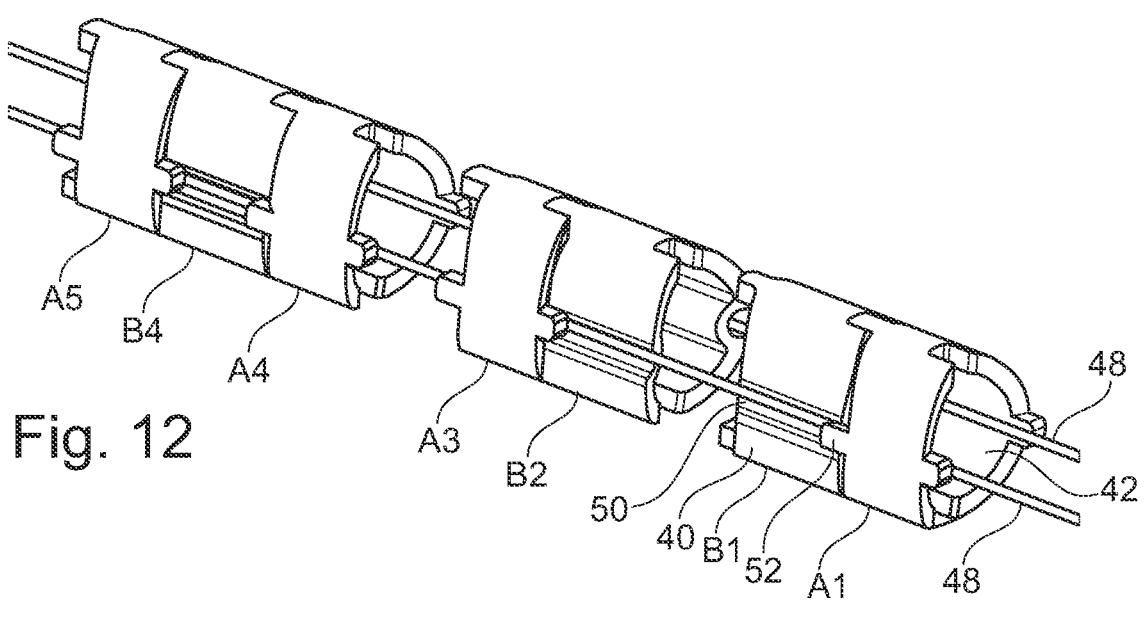
FIG. 12 is a perspective view of the assembly of intermediate bending segments shown in FIG. 10 with two intermediate bending segments removed for illustration purposes.

FIG. 11, which is a top view of the assembly of intermediate bending segments 36 shown in FIG. 10, shows one big inner lumen 74 and two steering wire passages 76, which are formed in the assembled state of the intermediate being segments 36. As can be best seen in FIG. 12, the steering wire portions 48 run on the inner circumferential side or surface 42 of the first intermediate segments A (A1, A2, A3, A4, A5) and on the outer circumferential side or surface 40 in axially extending grooves 50 of the second intermediate segments B (B1, B2, B3, B4) and keep the alternately arranged first intermediate segments A and second intermediate segments B together. The axially extending grooves 50 extend over the entire axial length of the second intermediate segments B1, B2, B3 and B4. In the assembled state of the intermediate segments 36 stabilizing protrusions 52 are arranged and accommodated in the axially extending grooves in which the steering wire portions 48 run.

Figure 13:
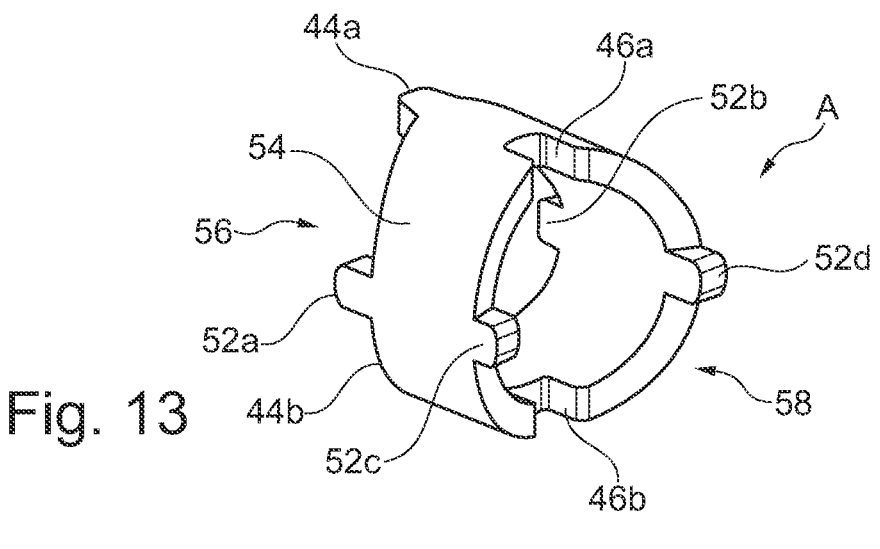
FIG. 13 is a perspective view of one first intermediate segment shown in FIG. 10.

FIG. 13 shows a perspective view of the first intermediate segment A according to the second embodiment. The first intermediate segment A comprises a tubular body 54. On a first axial end 56 of the tubular body 54 two hinge protrusions 44a, 44b and two stabilizing protrusions 52a, 52b are provided. On a second axial end 58 of the tubular body 54 two hinge recesses 46a, 46b and two stabilizing protrusions 52c, 52d are provided. The two hinge protrusions 44a, 44b provided on the first axial end 56 of the first intermediate segment A are arranged diametrically opposed with respect to a center axis of the first intermediate segment A. The two stabilizing protrusions 52a, 52b provided on the first axial end 56 of the first intermediate segment A are arranged diametrically opposed with respect to a center axis of the first intermediate segment A. The four protrusions (two hinge protrusions 44a, 44b and two stabilizing protrusions 52a, 52b) on the first axial end 56 are equally spaced in the circumferential direction. The two hinge recesses 46a, 46b provided on the second axial end 58 of the first intermediate segment A are arranged diametrically opposed with respect to a center axis of the first intermediate segment A.

The two stabilizing protrusions 52c, 52d provided on the second axial end 58 of the first intermediate segment A are arranged diametrically opposed with respect to a center axis of the first intermediate segment A. The two hinge recesses 46a, 46b provided on the second axial end 58 of the first intermediate segment A are axially aligned with the two hinge protrusions 44a, 44b provided on the first axial end 56 of the first intermediate segment A. The two stabilizing protrusions 52c, 52d provided on the second axial end 58 of the first intermediate segment A are axially aligned with the two stabilizing protrusions 52a, 52b provided on the first axial end 56 of the first intermediate segment A. Each hinge recess 46a, 46b is spaced by 90° in the circumferential direction from the two adjacent stabilizing protrusions 52c, 52d.

Figure 14:
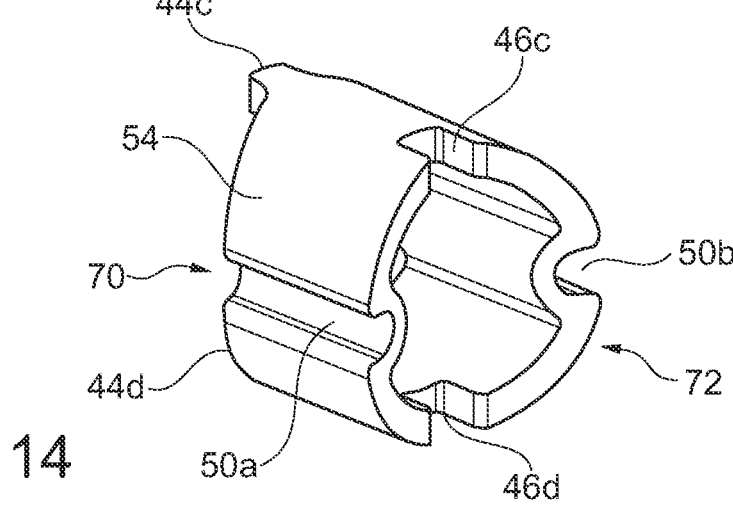
FIG. 14 is a perspective view of one second intermediate segment shown in FIG. 10.

FIG. 14 shows a perspective view of the second intermediate segment B according to the second embodiment. The second intermediate segment B comprises a tubular body 54. On a first axial end 70 of the tubular body 54 two hinge protrusions 44c, 44d are provided. On a second axial end 72 of the tubular body 54 two hinge recesses 46c, 46d are provided. Two axially extending grooves 50a, 50b extend from the first axial end 70 to the second axial end 72. The two hinge protrusions 44c, 44d provided on the first axial end 70 of the second intermediate segment B are arranged diametrically opposed with respect to a center axis of the second intermediate segment B. The two hinge recesses 46c, 46d provided on the second axial end 72 of the second intermediate segment B are arranged diametrically opposed with respect to a center axis of the second intermediate segment B. The two hinge protrusions 44c, 44d are axially aligned with the two hinge recesses 46c, 46d, i.e. a plane may be defined in which the two hinge protrusions 44c, 44d and the two hinge recesses 46c, 46d lie. The two axially extending grooves 50b are spaced by 90° in the circumferential direction from adjacent hinge protrusions 44c, 44d/hinge recesses 46c, 46d. The first intermediate segment A and the second intermediate segment B are assembled by putting the first axial end 70 of the second intermediate segment B onto the second axial end 58 of the first intermediate segment A or by putting the first axial end 56 of the first intermediate segment A onto the second axial end 72 of the second intermediate segment B.

Figure 15:
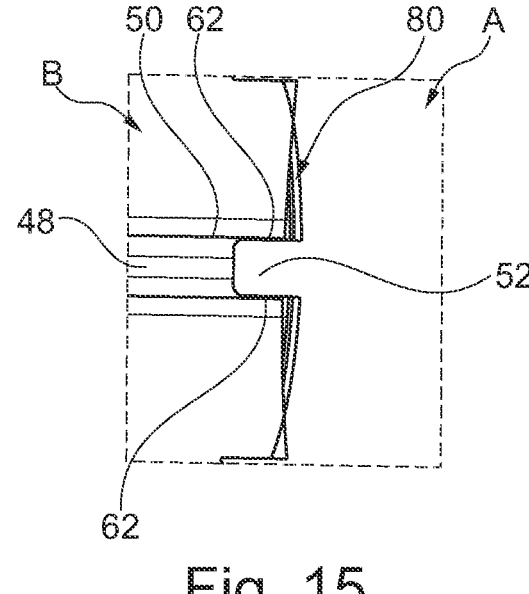
FIG. 15 shows a side view of a stabilizing protrusion of the first intermediate segment arranged and accommodated in an axially extending groove of the second intermediate segment.

In the assembled state the hinge protrusions 44 engage with the hinge recesses 46 to form hinges 43, and the stabilizing protrusions 52 of the first intermediate segments A are received in the axially extending grooves 50 of the second intermediate segments B to provide appropriate torsional/rotational stiffness. As can be seen in FIG. 15, the stabilizing protrusions 52 are adapted in size and shape to the axially extending grooves 50 such that they slide in the axially extending grooves 50 provided for the steering wire portions 48 and lock a rotation between adjacent intermediate segments. This is in particular achieved by the stabilizing protrusions 52 contacting both parallel leg portions 62 of the U-shaped recess 60 and leaving some space for the steering wire 48 radially further inside.

The stabilizing protrusions 52 of the second embodiment may have a tapered or rounded portion like the stabilizing protrusions 52 of the first embodiment. Such a radially inner tapered or rounded portion helps to avoid an engagement of the stabilizing protrusions 52 with the steering wire portions 48 when the bending section 10 is bent. In addition or alternatively, the stabilizing protrusions 52 may have a radially outer tapered or rounded portion, which helps to avoid that the stabilizing protrusions 52 project radially outward/laterally thus increasing the diameter of the bending section 10 when the bending section 10 is bent.

FIG. 15 further shows an angle or gap 80 between adjacent intermediate segments A, B, which defines a bending angle between the adjacent intermediate segments A, B. The angle or gap 80 may be varied along the proximal-distal direction for providing different bending angles at different positions in the proximal-distal direction.

Figure 16:
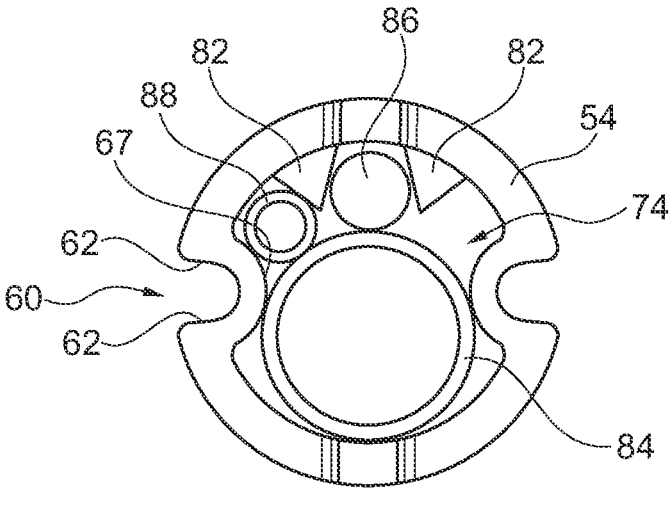
FIG. 16 shows a top view of a second intermediate segment having inner bulged portions.

FIG. 16 shows a variation of the second intermediate segment B according to the second embodiment. The second intermediate segment B comprises two inner bulged portions 82, which are formed integrally with the tubular body 54 of the second intermediate segment B. In the inner lumen 74 of the second intermediate segment B a large working channel tube 84 is arranged. The inner bulged portions 82 in combination with the working channel tube 84 and the projections 67 formed by the U-shaped recesses 60 respectively the axially extending grooves 50 serve to keep cables 86 or tubes 88 in place during bending of the bending section 10.

The outer diameter of the bending section 10, which corresponds to the outer diameter of the intermediate segment B shown in FIG. 16 is less than 3 mm and the working channel tube 84 has an inner diameter of 1.1 mm to 1.3 mm. The diameter of the working channel tube 84 is relatively large compared to the outer diameter of the bending section 10.

FIGS. 17 and 18 illustrate examples of the monitor 18, denoted by numerals 140 and 160. In FIG. 17, the monitor includes a housing 142 enclosing and supporting a display screen 144 and a video processing circuit (not shown). The display screen 144 may be a touch-screen. A cable socket 146 receives a cable connector of a cable of the endoscope 2 to establish a signal communication between the image sensor and the monitor. The monitor allows an operator to view an image captured by the image sensor. A medical device interface 148 is tailored to a specific endoscope technology, such as a type or model of image sensor, electronic circuits to encode other endoscope signals, configuration parameters of the image sensor, and the like. The medical device interface 148 is connected to the video processing circuit and can pre-process signals before conveying them to the video processing circuit. For example, the medical device interface 148 may deserialize a video signal or modify the size of the frames. Thus, the medical device interface 148 is technologically matched to a particular endoscope, and inclusion of the medical device interface 148 in the monitor 18, 140, 160 matches the endoscope to the monitor. As shown in FIG. 17, the monitor may comprise multiple cable sockets 146 and, correspondingly, multiple medical device interfaces 148, which may be coded to indicate which endoscope matches which medical device interface. Coding may be via symbols, colors, or both. Example medical device interfaces and codings are described in commonly owned U.S. Pat. Nos. 11,166,622 and 11,166,624, both issued Nov. 9, 2021 and incorporated herein by reference.

It might not be desirable to provide a video display screen with a touch screen, or it might be desirable to omit a display screen altogether. Omission of the display screen might be beneficial to take advantage of evolving video display technologies which improve resolution and reduce cost. Provision of exchangeable medical device interfaces allows for adoption of evolving image sensor and endoscope technologies, thus use of existing or future-developed external video displays could allow presentation of higher resolution or otherwise improved video. Use of external video displays could also leverage existing capital investments. Accordingly, in FIG. 18 the monitor 160 comprises a housing 162 supporting a video processing circuit (not shown), a medical device interface, and cable socket 146, but excludes a display screen, which is provided separately and is communicatively connectable to the monitor 160.

The following items are additional variations and examples of the embodiments described with reference to FIGS. 1 to 8.

1. Endoscope (2) comprising: an handle (4) or interface; and an insertion cord (6) configured to be inserted into a patient's body cavity and comprising an actively bendable bending section (10); the bending section (10) comprising a plurality of bending segments (32) including a proximal end segment (34), a plurality of intermediate segments (36) and a distal end segment (38); the plurality of intermediate segments (36) being separate annular or tubular segments made from a polymer material and having an outer circumferential side or surface (40) and an inner circumferential side or surface (42); the plurality of intermediate segments (36) comprising a plurality of first intermediate segments (A) and a plurality of second intermediate segments (B) being arranged alternately one after the other in a proximal-distal direction; wherein hinges (43) between the first intermediate segments (A) and the second intermediate segments (B) are formed by hinge protrusions (44) engaging in hinge recesses (46); wherein steering wires (48) run on the inner circumferential side or surface (42) of the first intermediate segments (A) and on the outer circumferential side or surface (40) in axially extending grooves (50) of the second intermediate segments (B) and keep the alternately arranged first intermediate segments (A) and second intermediate segments (B) together; and wherein the first intermediate segments (A) comprise stabilizing protrusions (52) arranged and accommodated in the axially extending grooves (50) of the second intermediate segments (B), in which the steering wires (48) run.

2. Endoscope (2) according to item 1, wherein the first intermediate segments (A) and the second intermediate segments (B) are adapted to each other such that, when joining the first intermediate segments (A) and the second intermediate segments (B) together alternately, the hinges (43) and passages (76) for the steering wires (48) are formed and the stabilizing protrusions (52) of the first intermediate segments (A) are inserted and guided into the axially extending grooves (50) of the second intermediate segments (B).

3. Endoscope (2) according to item 1 or 2, wherein no first intermediate segment (A) is connected to another first intermediate segment (A) and no second intermediate segment (B) is connected to another second intermediate segment (B), therefore no intermediate segment (36) being connected to an intermediate segment (36) being of the same type.

4. Endoscope (2) according to any one of the preceding items 1 to 3, wherein the steering wires (48) are alternately arranged radially inward with respect to a wall of the first intermediate segments (A) over an entire axial length of the first intermediate segments (A) and radially outward with respect to a wall of the second intermediate segments (B) over an entire axial length of the second intermediate segments (B).

5. Endoscope (2) according to any one of the preceding items 1 to 4, wherein seen in a cross-sectional view of the second intermediate segments (B) the axially extending grooves (50) are formed by interrupting a round outer contour of the second intermediate segments (B) by an essentially U-shaped recess (60) having two essentially parallel leg portions (62, 64) connected by a rounded portion (66).

6. Endoscope (2) according to item 5, wherein the rounded portion (66) is configured to accommodate the respective steering wire (48) running in the respective axially extending groove (50) and the two parallel leg portions (62, 64) are distanced and adapted to the respective stabilizing protrusion (52) of the first intermediate segment (A) such that the two parallel leg portions (62, 64) form guide portions arranged in close proximity to and axially guiding the respective stabilizing protrusion (52).

7. Endoscope (2) according to item 5 or 6, wherein said U-shaped recess (60) interrupting the circular outer contour of the second intermediate segments (B) on the outer circumferential side or surface (40) forms a projection (67) protruding inwardly on the inner circumferential side or surface (42).

8. Endoscope (2) according to any one of the preceding items 1 to 7, wherein the stabilizing protrusions (52) have at least one tapered or rounded surface preventing, when the bending section (10) is bent, an engagement of the stabilizing protrusions (52) with the radially further inward steering wires (48) and/or a lateral or radially outward protruding of the stabilizing protrusions (52).

9. Endoscope (2) according to any one of the preceding item 1 to 8, wherein the endoscope (2) is a small outer diameter endoscope having an outer diameter of the insertion cord (6) of less than 3 mm in case of a one-plane bending endoscope and having an outer diameter of the insertion cord (6) of less than 5 mm in case of a two-plane bending endoscope.

10. Endoscope (2) according to any one of the preceding items 1 to 9, wherein the endoscope (2) is a one-plane bending endoscope configured to bend in two opposite direction, wherein each first intermediate segment (A) comprises two hinge protrusions (44), two hinge recesses (46) and four stabilizing protrusions (52) and each second intermediate segment (B) comprises two hinge protrusions (44), two hinge recesses (46) and two axially extending grooves (50).

11. Endoscope (2) according to any one of the preceding claims 1 to 9, wherein the endoscope (2) is a two-plane bending endoscope configured to bend in four directions, wherein each first intermediate segment (A) comprises four hinge protrusions (44) and four stabilizing protrusions (52) and each second intermediate segment (B) comprises four hinge recesses (46) and four axially extending grooves (50).

12. Endoscope (2) according to any one of the preceding items 1 to 11, wherein the plurality of intermediate segments (36) are molded, in particular injection-molded, segments.

13. Endoscope (2) according to any one of the preceding items 1 to 12, wherein an angle or a gap (80) between adjacent segments (A, B) of the plurality of intermediate segments (36) is varied along the proximal-distal direction for providing different bending angles at different positions in the proximal-distal direction.

14. Endoscope (2) according to any one of the preceding items 1 to 13, wherein at least one of the plurality of intermediate segments (36) comprises an inner bulged portion (82) keeping cables (86) and/or tubes (88) arranged in an inner lumen (74) of the at least one of the plurality of intermediate segments (36) in place during bending of the bending section (10).

15. System comprising: an endoscope (2) according to any one of the preceding items 1 to 14; and a monitor (18) connectable to the endoscope (2).

LIST OF REFERENCE SIGNS

2 endoscope
4 handle
6 insertion cord
8 insertion tube
10 bending section

12 distal tip unit
14 light emitting device
16 imaging device
18 monitor
20 working channel
22 access port
24 first steering wheel
26 second steering wheel
28 gas/water injection valve
30 suction valve
32 bending segments
34 proximal end segment
36 intermediate segments
38 distal end segment
40 outer circumferential side or surface
42 inner circumferential side or surface
43 hinge
44 hinge protrusion
46 hinge recess
48 steering wires
50 axially extending grooves
52 stabilizing protrusions
54 tubular body
56 first axial end (of intermediate segment A)
58 second axial end (of intermediate segment A)
60 U-shaped recess
62 first leg portion
64 second leg portion
66 rounded portion
67 projection
68 recessed body
70 first axial end (of intermediate segment B)
72 second axial end (of intermediate segment B)
74 inner lumen
76 steering wire passage
78 lever
80 angle or gap
A first intermediate segment
B second intermediate segment

I claim:

1. An endoscope comprising:

a handle or interface; and an insertion cord configured to be inserted into a patient's body cavity and comprising an insertion tube and a bending section extending distally from the insertion tube, the bending section comprising:

segments including a proximal end segment, a distal end segment, and intermediate segments between the proximal end segment and the distal end segment, the intermediate segments being separate annular or tubular segments, each of the intermediate segments having a body with an outer circumferential side or surface and an inner circumferential side of surface, the inner circumferential surface defining an inner lumen, the intermediate segments comprising first intermediate segments and second intermediate segments, the first intermediate segments and the second intermediate segments arranged alternately one after the other in a proximal-distal direction, each of the first intermediate segments including stabilizing protrusions extending longitudinally from the body, and each of the second intermediate segments including axially extending grooves, the axially extending grooves extending lengthwise and radially inward from the outer circumferential surface of the body toward, but not reaching, the inner circumferential surface,

wherein hinges between the first intermediate segments and the second intermediate segments are formed by hinge protrusions engaging in hinge recesses, wherein steering wire portions run on the inner lumen of the first intermediate segments and within the axially extending grooves of the second intermediate segments and keep the first intermediate segments and the second intermediate segments together, and wherein the stabilizing protrusions of the first intermediate segments are accommodated in the axially extending grooves of the second intermediate segments.

2. The endoscope of claim 1, wherein the first intermediate segments include the hinge protrusions, the hinge protrusions extending longitudinally from the body, and wherein the second intermediate segments include the hinge recesses.

3. The endoscope of claim 2, wherein the hinge recesses are longitudinally adjacent the axially extending grooves.

4. The endoscope of claim 3, wherein the endoscope is a two-plane bending endoscope, and wherein each of the first intermediate segments include two of the hinge protrusions and two of the stabilizing protrusions extending distally from the body and two of the hinge protrusions and two of the stabilizing protrusions extending proximally from the body.

5. The endoscope of claim 4, wherein the insertion cord has an outer diameter of less than 5 mm.

6. The endoscope of claim 4, wherein the two of the hinge protrusions extending distally from the body are offset 90 degrees from the two of the hinge protrusions extending proximally from the body.

7. The endoscope of claim 3, wherein the endoscope is a one-plane bending endoscope, wherein each of the first intermediate segments include two of the hinge protrusions and two of the stabilizing protrusions extending distally from the body and two of the hinge protrusions and two of the stabilizing protrusions extending proximally from the body, and wherein the two of the hinge protrusions extending distally from the body are longitudinally aligned with the two of the hinge protrusions extending proximally from the body.

8. The endoscope of claim 7, wherein the insertion cord has an outer diameter of less than 3 mm.

9. The endoscope of claim 1, wherein the stabilizing protrusions of the first intermediate segments are inserted into the axially extending grooves of the second intermediate segments, and wherein the hinge protrusions of the first intermediate segments are inserted into the hinge recesses of the second intermediate segments.

10. The endoscope of claim 9, wherein the hinge recesses are longitudinally adjacent the axially extending grooves.

11. The endoscope of claim 1, wherein each of the first intermediate segments is only adjacent to one or two of the second intermediate segments.

12. The endoscope of claim 1, wherein the steering wire portions are alternately arranged radially inward with respect to a wall of the first intermediate segments over an entire axial length of the first intermediate segments and radially outward with respect to a wall of the second intermediate segments over an entire axial length of the second intermediate segments.

13. The endoscope of claim 1, wherein in a cross-sectional view of the second intermediate segments the axially extending grooves are formed by interrupting a round outer contour of the second intermediate segments with a recess having opposing surfaces and a bottom surface connecting the opposing surfaces.

14. The endoscope of claim 13, wherein the opposing surfaces are parallel and the bottom surface is rounded.

15. The endoscope of claim 13, wherein the opposing surfaces are distanced and configured to be in close proximity to, and axially guiding, the stabilizing protrusion.

16. The endoscope of claim 15, wherein the axially extending grooves extend to a projection protruding inwardly on the inner circumferential side or surface.

17. The endoscope of claim 16, wherein each of the stabilizing protrusions has a tapered or rounded surface preventing, when the bending section is bent, engagement of the stabilizing protrusion with the steering wire portions.

18. The endoscope of claim 16, wherein each of the stabilizing protrusions has a tapered or rounded surface preventing, when the bending section is bent, engagement of the stabilizing protrusion with a lateral or radially outward protruding of the stabilizing protrusions.

19. The endoscope of claim 1, wherein the endoscope is configured to bend in a single plane, and wherein the insertion cord has an outer diameter of less than 3 mm.

20. The endoscope of claim 19, wherein the endoscope is configured to bend in two opposite directions, wherein each of the first intermediate segments comprises two hinge protrusions, two hinge recesses and four stabilizing protrusions, and wherein each of the second intermediate segments comprises two hinge protrusions, two hinge recesses and two axially extending grooves.

21. The endoscope of claim 1, wherein the intermediate segments are molded of polymeric material.

22. The endoscope of claim 1, wherein an angle or a gap between adjacent of the intermediate segments is varied along the proximal-distal direction for providing different bending angles at different positions in the proximal-distal direction.

23. The endoscope of claim 1, wherein at least one of the intermediate segments comprises an inner bulged portion keeping cables and/or tubes arranged in the inner lumen of the at least one of the intermediate segments in place during bending of the bending section.

24. A visualization system comprising:
the endoscope of claim 1; and
a monitor connectable to the endoscope.

* * * * *